United States Patent
Bushway

[19]

[11] Patent Number: 5,846,081
[45] Date of Patent: Dec. 8, 1998

[54] COMPUTERIZED INSTRUMENT PLATFORM POSITIONING SYSTEM

[76] Inventor: Geoffrey C. Bushway, 10191 Sugar Creek Dr., Pensacola, Fla. 32514

[21] Appl. No.: 643,578

[22] Filed: May 6, 1996

Related U.S. Application Data

[60] Provisional application No. 60/002,689 Aug. 23, 1995.

[51] Int. Cl.[6] .................................................. A61C 5/00
[52] U.S. Cl. .............................. 433/215; 433/72; 433/223
[58] Field of Search ................................... 433/72, 75, 68, 433/29, 215, 223, 229; 368/168, 474, 475, 414

[56] References Cited

U.S. PATENT DOCUMENTS

| | | | |
|---|---|---|---|
| 4,411,626 | 10/1983 | Becker et al. | 433/223 |
| 4,478,580 | 10/1984 | Barrut | 433/223 |
| 4,575,805 | 3/1986 | Moermann et al. | 433/223 X |
| 4,941,826 | 7/1990 | Loran et al. | 433/223 X |
| 5,224,049 | 6/1993 | Mushabac | 433/223 X |
| 5,383,752 | 1/1995 | Rheinberger et al. | 433/223 X |

*Primary Examiner*—Nicholas D. Lucchesi

[57] ABSTRACT

A precision instrumentation platform carrying a tool, such as a scanner or drill, on a computer-controlled robotic arm is controlled by a robotic type positioning system. The scanner of the platform makes a three dimensional tomographic type scan of the area being diagnosed and a computer image is formed. A drill, or other treatment modality of the instrumentation platform, is controlled to treat the affected area. In the preferred embodiment of the invention, computer-controlled hydraulic pumps control vertical movement and rotation of the robotic arm and the instrumentation platform. These pumps adjust fluid volummes in various chambers to position the platform either for the purpose of making the scan or performing the treatment. As fluid volummes change, pistons move, and the platform follows a computer-directed path. Positional sensors, along with connecting torque systems and control systems create a multi-loop servo-system that guides the platform.

18 Claims, 4 Drawing Sheets

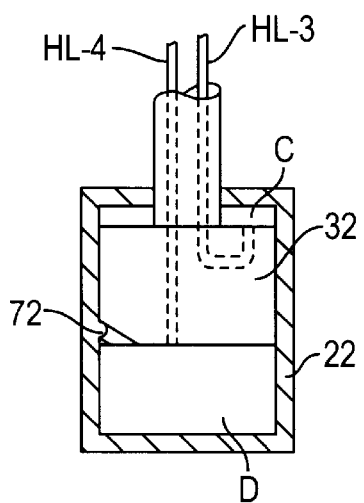
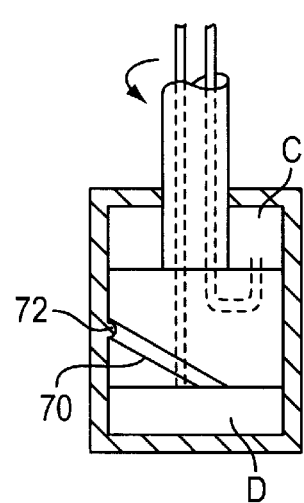
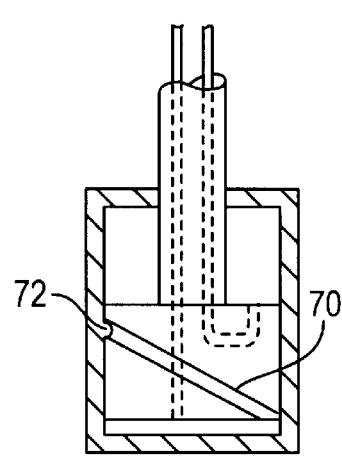
FIG. 5A    FIG. 5B    FIG. 5C
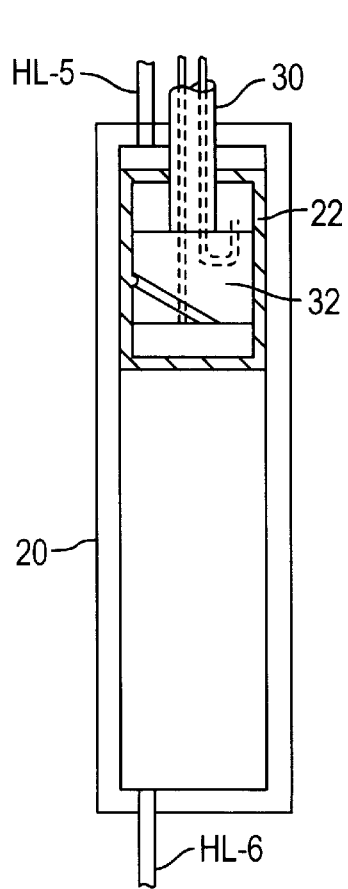
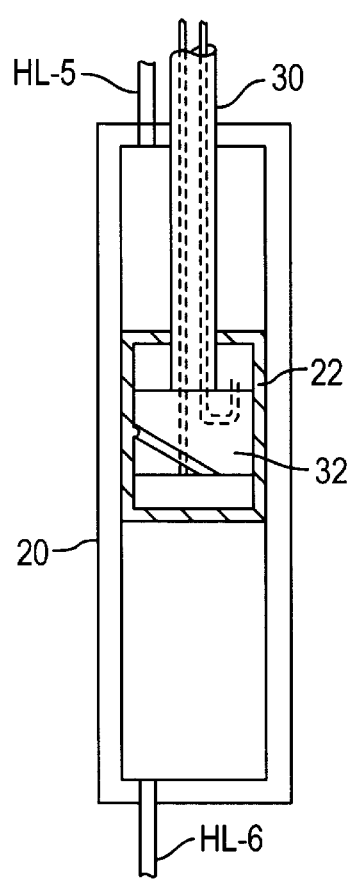
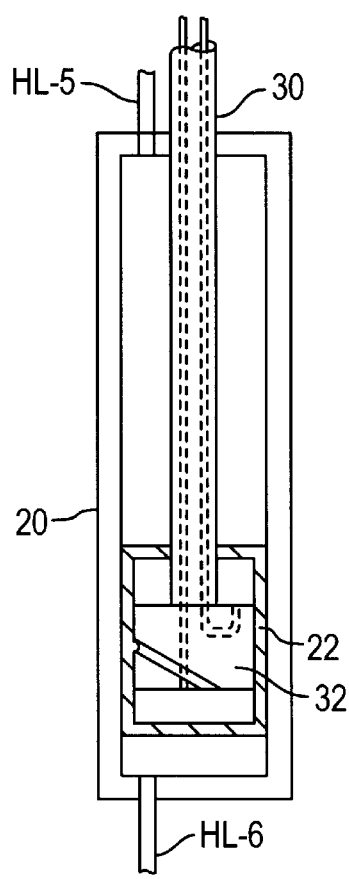
FIG. 6A    FIG. 6B    FIG. 6C

COMPUTERIZED INSTRUMENT PLATFORM POSITIONING SYSTEM

RELATED APPLICATION

This application is a continuation-in part of Provisional application Ser. No. 60/002,689 filed Aug. 23, 1995.

FIELD OF THE INVENTION

The present invention relates to a computer controlled robotic type arm system that is usable for positioning an instrument platform, such as a scanner and dental instrument for treating teeth, on a three dimensional basis.

BACKGROUND OF THE INVENTION

Signs and symptoms of dental disease, such as dental caries and dental root problems, are frequently confusing to the dental practitioner. No satisfactory tomographic dental scanner or drill is currently believed to exist to permit inspection, evaluation and treatment of teeth on a three-dimensional basis. Dentists and dental consumers currently use dental X-rays and other instruments based on technology largely developed in the 1950's and prior years for diagnosis and for treatment.

Diagnostic aids currently in use based on this existing technology include, for example, a two-dimensional dental X-ray, an electric pulp tester, a mouth mirror, a light probe such as a flashlight and an ordinary dental probe. Frequently, these aids supply inconclusive information. For example, a patient with dental pain often cannot tell which tooth hurts. When the source of the pain is not obvious to the dentist, the patient's options are limited. The dentist can either: make an educated guess as to which tooth is the offending tooth and treat the educated guess; treat all teeth that could be the offender, commonly known as the 'shotgun' treatment method; or tell the patient to continue to suffer the inconvenience and wait until he or she (the patient) can identify the painful tooth, that is, when the pain localizes to the offending tooth. None of these approaches is truly satisfactory to either the patient or the dentist performing the treatment.

For today's dental consumer with a toothache, guessing which tooth is to be extracted, filled, or root-canaled is unsatisfactory. Waiting for the pain to localize is discomfiting and waiting may not be successful since the pain may never localize. If forced to wait for the to pain localize, the patient with a toothache is little comforted knowing that his/her parents (or grandparents) probably faced the same dental dilemma since their dentists used similar diagnostic aids.

If the initial treatment is not successful, because of mis-diagnosis, re-treatment must still rely on a second arbitrary reassessment using the same diagnostic aids used initially. Error of treatment in the second try is still possible and the patient sometimes must undergo several rounds of treatment before the problem is finally successfully diagnosed and treated. Accordingly, a need exists for an apparatus which will enable a dentist to more accurately diagnose and treat patients.

Further, the treatment of a dental problem still, in large part, relies on long existing technology basically relying on the skill of the dentist to manipulate hand tools, such as drills, picks, reamers and other instruments. The manipulation of the instruments is carried out based on visual observation by the dentist of the area being treated with some reliance based on information obtained from X-rays.

BRIEF DESCRIPTION OF THE INVENTION

The present invention relates to a miniaturized precision instrumentation platform carrying a tool such as a scanner and drill on a computer-controlled robotic arm that can be used to both diagnose and treat a patient, as well as for other purposes. The instrumentation platform is controlled by a robotic type positioning system. The scanner of the platform makes a three dimensional tomographic type scan of the area being diagnosed and a computer image is formed of an area to be treated. Based upon the information obtained from the scan, which provides information both for diagnosis and for treatment, the drill or other treatment modality of the instrumentation platform is controlled to treat the affected area.

In the preferred embodiment of the invention, computer-controlled hydraulic pumps control vertical movement and rotation of the robotic arm and the instrumentation platform. These pumps adjust fluid volummes in various chambers to position the platform either for the purpose of making the scan or performing the treatment. As fluid volummes change, pistons move, and the platform follow a computer-directed path. Positional sensors, along with connecting torque systems and control systems create a multi-loop servo-system that guides the platform.

The scanner generates a computer image that describe the contours and substructure of a sample, such as selected areas of one or more teeth. If desired, a microcomputer can compare the image of the scanned sample with a database of known samples to aid in a diagnosis. The information obtained from the scanned sample can be further used to control the movement of the platform and the mounted tool to appropriately treat the area. The scanner-and-drill platform design can be used with various CIM (Computer Integrated Manufacture) peripherals.

OBJECTS OF THE INVENTION

It is therefore an object of the invention to provide a computerized system for controlling the positioning of an instrument platform with an attached tomographic scanner.

A further object is to provide a miniaturized computer controlled system for treating teeth.

An additional object is to provide a system for positioning a platform for carrying an instrument, such as a scanner or a cutting tool, that can be used in as restricted location, such as the mouth of a patient whose teeth are being treated.

Yet another object is to provide a system for controlling the position of an instrument platform that carries a scanner to diagnose an object and another type of tool for treating the diagnosed object.

BRIEF DESCRIPTION OF THE DRAWINGS

Other objects and advantages of the present invention will become more apparent upon reference to the following specification and annexed drawings in which:

FIGS. 5a, 5b and 5c are views of the assembly of FIG. 4 shown partly broken away, in different positions of rotation; and FIGS. 6a, 6b and 6c are views of the assembly of FIG. 3, shown partly broken away, in different depth positions.

DETAILED DESCRIPTION OF THE INVENTION

Figure 1:
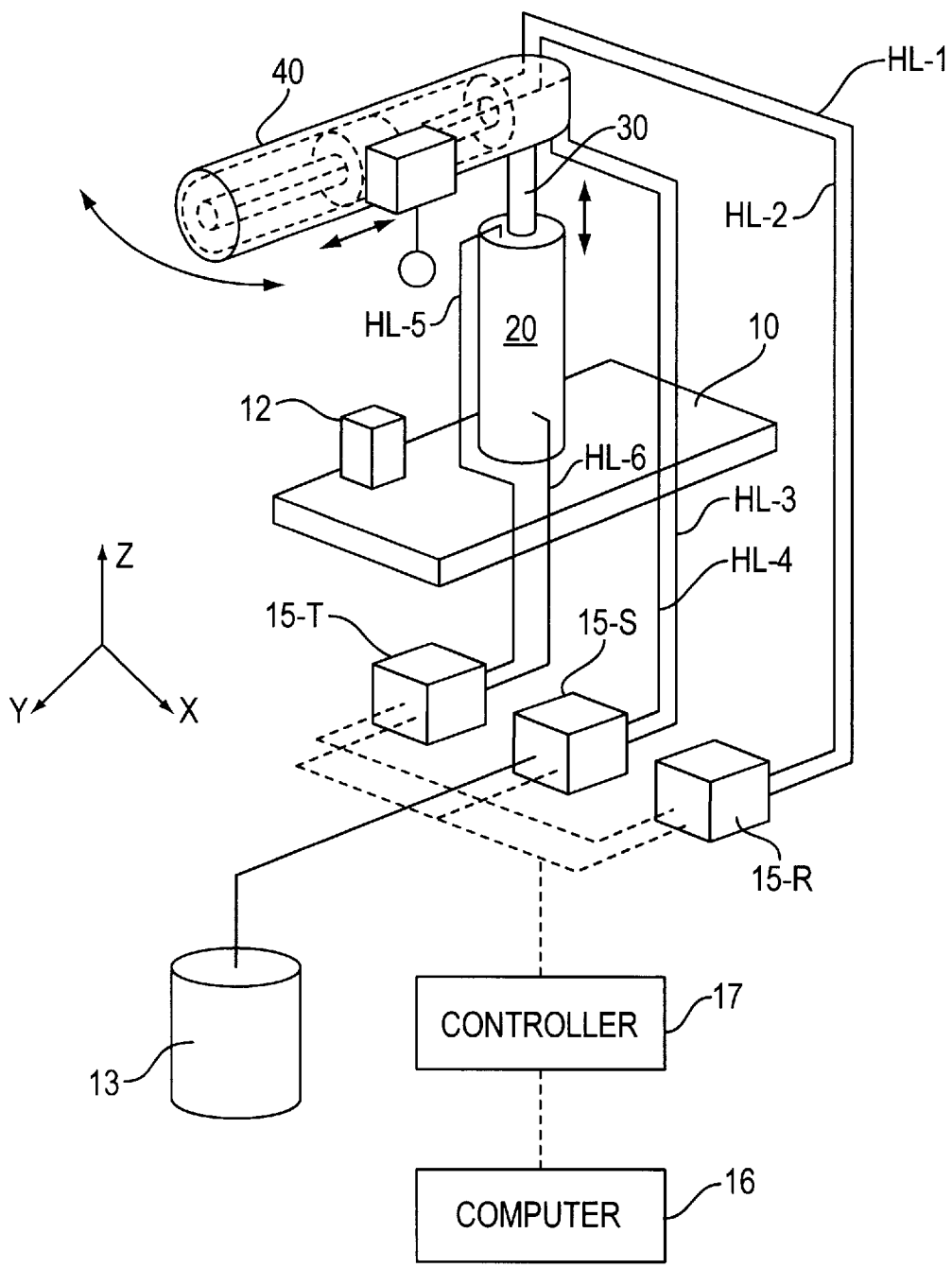
FIG. 1 is an overall perspective schematic view of the system.
Figure 2:
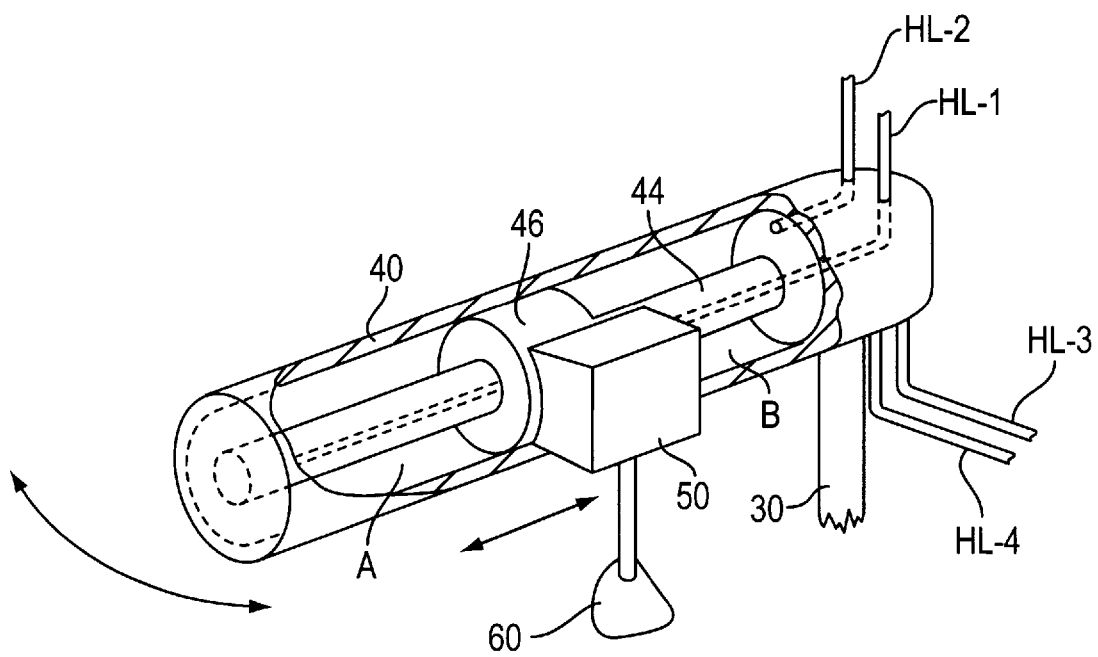
FIG. 2 is a perspective view of the transporter housing shown partly broken away.

Referring to the drawings, FIG. 1 illustrates the overall layout of the system and FIG. 2 the internal details of the transporter housing. For understanding the system, it should be considered that the various components are sized to meet the application. For example, the robotic arm system components can be scaled as appropriate to accommodate relatively small applications, such as being used in the mouth of a dental patient, or in larger industrial type applications.

In FIGS. 1 and 2, there is a support base 10 that conforms to the location at which the robotic arm system is to be used. For example, if it is to be located in the mouth of a patient receiving dental treatment, the base 10 can be releasably affixed to a tooth by a suitable fastening system, for example, a tension-activated rubber dam clamp. That is, base 10 can be a releasable clamp. When the system is used for larger scale activities, the base 10 can be a stationary platform.

A main cylinder 20 is mounted on base 10. As described below, cylinder 20 houses a number of components. In FIGS. 1 and 2 the vertical axis of cylinder 20 illustratively is shown extending in the vertical (Z) direction and other components, such as base 10, located at 90° relative to the cylinder 20, in a generally horizontal (X-Y) plane. Of course, the base 10 can be mounted at an angle relative to the horizontal to locate all of the other system components in planes related to said angle. Alternatively, the base 10 can be maintained in the generally X-Y plane and the cylinder 20 can be positioned at an angle other than 90° relative to the X-Y plane.

The lower end of an alignment support 30 is disposed in and supported by cylinder 20 for movement coaxial with the cylinder, in a vertical direction as shown, in a manner described below. Also as described below, the alignment support 30 is rotatable. That is, it rotates in the X-Y plane. A horizontally disposed transporter housing 40 is mounted on the upper end of the alignment support 30. Transporter housing 40 has a central shaft 44 mounted internally along its length. It also includes a slide 46 that rides on a shaft 44 to form within housing 40 chambers A and B each of which receives fluid in a controlled manner. The fluid in chambers A and B communicates with and reacts on slide 46 on the central support shaft 44 and variation of the fluid volume in chambers A and B causes slide 46 to move in either direction along the length of the shaft.

A mount, or platform, 50 external of housing 40 is connected to central slide 46. Slide 46 and platform 50 form a central slide complex. Platform 50 is moved along the length of transporter housing 40 in accordance with the movement of the slide 46. The coupling between the slide 46 and platform 50 can be by any suitable mechanical means through the housing 40, with appropriate seals, by magnetic coupling, etc.

Platform 50 carries a tool 60, which can be, for example, a scanner device or a working tool such as a mechanical drill or ultrasonic cutting device. The scanner device can be of any suitable type, such as X-ray, digital radiography, thermal, ultrasonic, computerized tomography (CAT), or any combination thereof. The scanner preferably has the capability of producing a tomographic image of the object or sample being scanned and would have an associated computer to produce the image. The image data of the object obtained from the scanner is applied to the associated computer that processes the acquired data using mathematical algorithms according to selected parameters and generates a reconstructed tomographic image of the sample. The computer generated image is used for visualization and for diagnosis of the object as well as for treatment by positioning of a tool such as a drill to physically treat the object. Suitable energy sources for and types of scanner include lasers, thermal energy, MRIs and CTs (X-rays). Sometimes due to the nature of the sample, for example when imaging a tooth, tomographic analysis of a sample requires a combination of scanning media and image reconstruction algorithms.

If the tool 60 is a drill or other similar mechanical work implement, then the necessary drive source for the tool, such as a motor or turbine drive, is mounted on or within housing 40 or is mounted externally to housing 40 and connected, for example, by a conduit or sleeve to housing 40. In the embodiment shown in FIGS. 1 and 2 the scanner and the work implement are interchanged as needed or there can be separate positioning systems for each. Alternatively, a second platform like platform 50 can be added on the transporter housing 40 and separately controlled so that the same transporter housing can accommodate both a scanner and a work implement.

Tool 60 is to be positioned in the X, Y, and Z directions by the robotic arm system relative to an object sample 12, for example a tooth, which is to be scanned or worked on by tool 60. To accomplish this, the transporter housing 40 is moved vertically in the Z direction and rotated in the X-Y plane by mechanisms, to be described, in the main cylinder 20 and alignment support 30. As previously explained, the platform 50 is moved bi-directionally along the length of the transporter housing 40 in the X-Y plane. This combination of movements provides a wide variety of positioning locations for the tool 60.

The system is powered, in the preferred embodiment illustrated, by hydraulic fluid supplied from a reservoir 13 (FIG.1) to three bi-directional variable speed, variable capacity pumps 15-R, 15-S and 15-T. Operation of the pumps 15 is controlled by signals supplied from a computer 16. It is preferred that the same computer be used for processing the acquired image information. Computer 16 operates pumps 15 through a controller 17 which converts the computer's electrical signals into signals that control the operating time, direction and fluid supply volume of each of the pumps 15. The fluid can be either hydraulic or air and the fluid flow in supply lines HL, which preferably are flexible, is bi-directional.

The computer 16 can produce pump control signals from a stored program, such as stored on a disk or other memory device, to position tool 60. For example, when using the scanner the computer can receive signals from a suitable manually operated positioning device such as a mouse or a joystick. Also, the computer operator can actuate the pumps 15 utilizing a generalized database stored computer image template of the area being scanned or a generalized computer image of the type of sample. This operates the platform 50 to position the scanner to obtain the necessary data for forming the tomographic image. The pump control signals can be produced from a tomographic image of the object 12 being worked on. Computer programs can be used to rotate and otherwise manipulate a scanner's tomographic image of the object sample.

Once the image of the object is formed, it is used for diagnosis purposes and also to position platform 50 which now carries a working tool. The manual location by an operator of a cursor or other type marker on the computer image produces the signals for setting the position of the working tool relative to the object sample 12 and the operation of such tool on the object. Alternatively, the working tool can be automatically positioned by data from the image such as, for example, different color areas that correspond to portions of the object to be treated.

Computer 16 receives feedback control signals relative to the actual X, Y and Z positional coordinates of the tool 60, platform 50 and transporter housing 40 by suitable sensors (not shown) which can be of any conventional type, such as mechanical, electro-optical, etc., that are placed on the platform, tool and at other locations in the area being worked on. This ensures proper positioning of the tool 60 relative to the object sample in accordance with the instructions given by the computer. That is, any error in the sensed position of the tool relative to its computer designated position causes the computer to produce pump control error correction signals to properly position the tool. This is a conventional servo-loop operation.

Pump 15-R supplies fluid to and extracts fluid from chambers A and B of transporter housing 40 over fluid lines HL-1 and HL-2. As seen in FIGS. 1 and 2, the fluid lines HL-1 and HL-2 enter the end of the transporter housing 40 at which the support 30 is located. Line HL-1 communicates with chamber A and line HL-2 extends through the central shaft 44 to communicate with chamber B. Any other suitable fluid supply arrangement can be used. Movement of the central slide complex and platform 50 follows fluid volume changes in transporter housing chambers A and B. For example, when chamber B fills and chamber A empties, the central slide complex 46 moves a distance $\Delta xy$ away from the alignment support 30. Conversely, filling chamber A and emptying chamber B moves the central slide complex 46 a distance $\Delta xy$ toward the alignment support. As the central slide complex 46 slides along the length of the length of the transporter housing 40 it carries the mount 50 and the tool 60.

FIGS. 3–6 show the components for rotating the transporter housing 40 and mount 50 and for moving it vertically. A sub-cylinder 22 is vertically slidable within and along the interior of main cylinder 20. The lower end of alignment support shaft 30 is connected to a piston 32 that moves both vertically and rotationally within the sub-cylinder 22. Sub-cylinder 22 has a chamber C above and a chamber D below the alignment support shaft piston 32. The interior of the outer main cylinder 20 has a chamber E above and a chamber F below the sub-cylinder 22.

Figure 3:
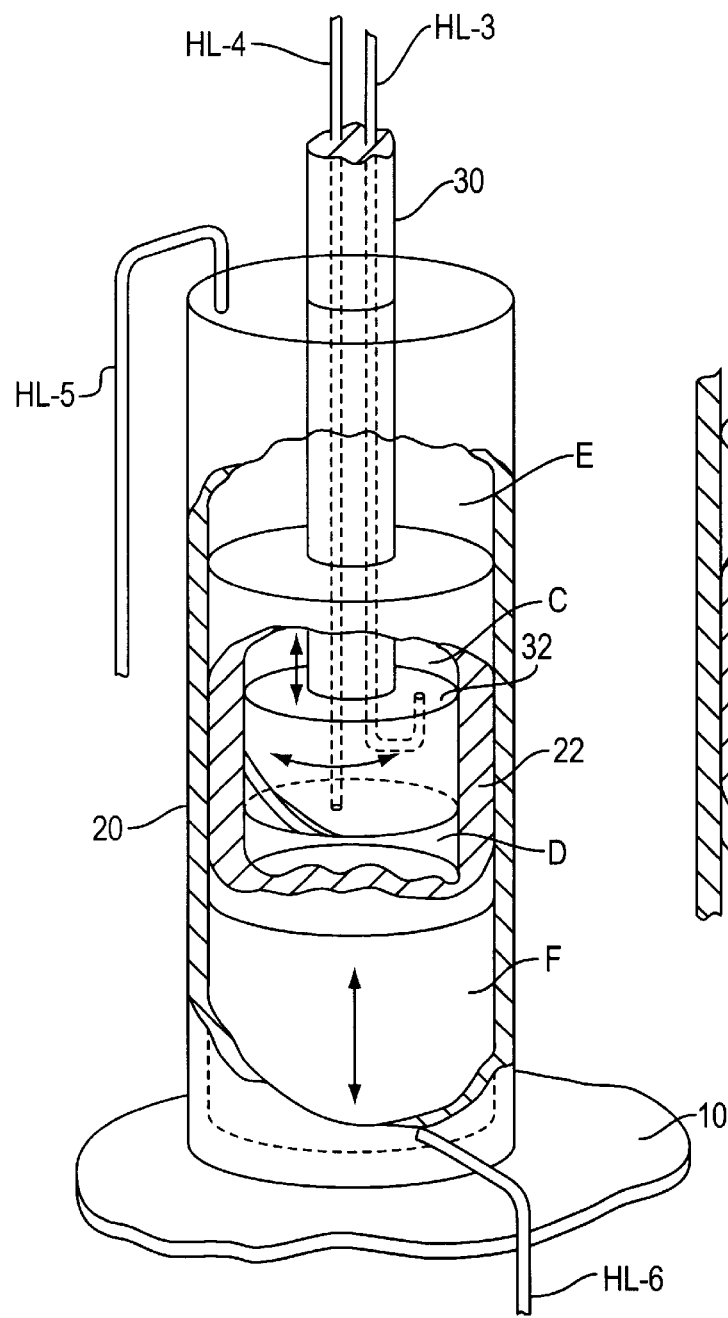
FIG. 3 is a plan view, partly broken away of the main support cylinder.
Figure 4:
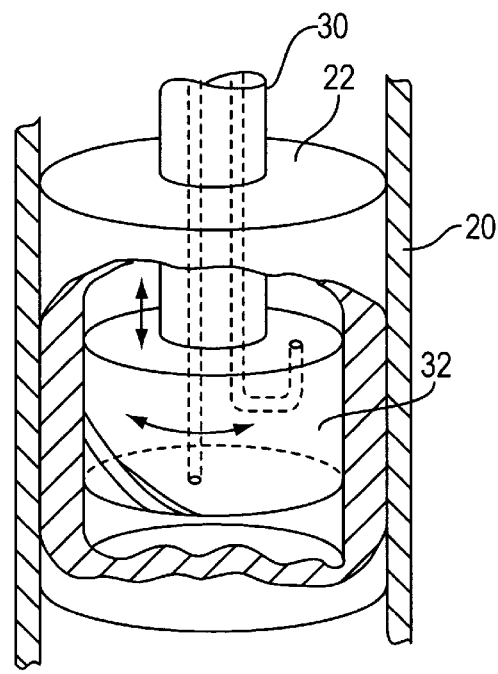
FIG. 4 is a plan view, partly broken away of the assembly for providing rotational movement of the platform transporter.

The microcomputer 16 controls pump 15-S to regulate the fluid volume in each of the sub-cylinder 22 chambers C and D over lines HL-3 and HL-4. It also controls pump 15-T to regulate over lines HL-5 and HL-6 fluid volume in chambers E and F in main cylinder 20. As seen in FIGS. 2–4, the fluid lines HL-3 and HL-4 enter the end of the transporter housing 40 and extend downward through the support shaft 30. The end of line HL-3 is shown extending into the piston 32 and then turning upwardly for communicating with the chamber C. Line HL-4 extends through the piston 32 to communicate with the chamber D. Other suitable types of fluid supply arrangements can be used. For example, the lines HL-3 and HL-4 can extend directly into alignment support shaft 30 rather than passing through transporter housing 40 and the line HL-3 can communicate with chamber C directly through the support shaft 30 rather than entering the piston 32.

Changing fluid volume in chambers E and F causes sub-cylinder 22 to move vertically up and down within main cylinder 20 along the Z-axis by a distance $\Delta z_1$. As sub-cylinder 22 moves vertically, it carries with it the alignment support 30 and the connected transporter housing 40 as well as the tool 60 carried by the platform 50. An indexing guide (not shown in FIGS. 3–6) guides the linear movement of sub-cylinder 22 along the Z-axis within cylinder 20. The amount of vertical displacement $\Delta z_1$ of housing 40 and tool 60 that it carries on mount 40 is determined by the fluid pressures in chambers E and F. The distance $\Delta z_1$ determines the ultimate location of tool 60 on the (vertical) Z-axis. If a drill is being used as the tool, then this distance determines the depth of cut.

Changing the fluid volume in chambers C and D of the sub-cylinder 22 under control of computer 16 and pump 15-S causes the alignment support piston 32 to move vertically within sub-cylinder 22. Vertical movement of piston 32 within sub-cylinder 22 is translated into rotational motion of the piston that produces rotation of the alignment support 30 in the X-Y plane, thereby rotating transporter housing 40 and tool 60 in the X-Y plane.

The angle of rotation of the alignment support shaft 30 and connected components is related to the vertical distance of movement of support piston 32 as it travels a distance $\Delta z_2$. As seen in FIGS. 5a–5c, the outer surface of the alignment support piston 32 within the sub-cylinder 22 has a helical thread 70. The interior wall of sub-cylinder 22 has a pawl 72 that engages with the thread 70 on piston 32. The locations of the pawl and thread can be reversed with thread 70 being on the sub-cylinder 22 and the pawl on the piston 32. When the alignment support piston 32 moves vertically within sub-cylinder 22, in accordance with the fluid pressure in chambers C and D, the pawl 72 engages the thread 70 on the alignment support piston 32 and the piston is caused to rotate thus rotating the alignment support 30 and the transporter housing 40. In these figures, for clarity of explanation, the thread 70 and pawl 72 are shown greatly enlarged. In practice the thread is finer, has more turns and is more compressed as needed to fit a particular application.

The force applied to piston 32 as well as the size, shape and pitch of thread 70 and the shape of pawl 72 are selected to operate so that the piston 32 rotates smoothly and the thread does not jump over the pawl. The alignment support 30 and transporter housing 40 rotate based on the amount of vertical movement $\Delta z_2$ of alignment support piston 32 and the thread 70 design (pitch) on the piston.

The rotation of the alignment support 30 and connected transporter housing 40 in the X-Y plane is explained by referring to FIGS. 5a through FIG. 5c. In this explanation, consider that $\Delta z_1$ remains constant, that is, the vertical position of sub-cylinder 22 is held fixed. As chamber C of sub-cylinder 22 fills, chamber D empties, and piston 32 moves vertically within sub-cylinder 22 and rotational motion of piston 32 is produced due to the interaction of thread 70 and pawl 72.

In the illustrative dental example being described, the rotational angle $\Theta$ of the alignment support 30 varies continuously throughout a range from 0° (FIG. 5a) to about 150° (FIG. 5c). FIG. 5b shows an approximate mid-point. Filling chamber D and emptying chamber C begins a return to the position shown in FIG. 5a. Because sub-cylinder 22 pawl 72 engages the thread 70 on the alignment support piston 32, the rotation parameter (angle $\Theta$) is a function of the linear vertical distance displacement parameter $\Delta z_2$. This distance is controlled by the amount of fluid in the two chambers C and D between the extremes of being full or empty.

Several refinements can be made to control the angle of rotation Θ of the alignment support shaft 30 more precisely. These include, for example, changing the machining tolerance of thread 70, for example, from ±0.001 inches to ±0.0001 inches. Another way is to keep the same tolerance (for example, ±0.001 inches), and increase the height of piston 32, i.e., use a looser pitch (more widely spaced) thread 70. A further technique is to hold the thread tolerance and the height of piston 32 constant and increase the diameter of the portion of the alignment support piston 32 on which the thread is formed.

Changes in $\Delta z_2$, to rotate the transporter housing 40 in the X-Y plane, cause small changes in $\Delta z_1$, the Z axis position of the housing. For example, in FIG. 5, if $\Delta Z_2$ varies on a scale from 0 (minimum as shown in FIG.5a) to 1 (maximum as shown if FIG. 5c), then angle Θ varies from 0° to 150° degrees. The vertical distance $\Delta Z_1$ that sets the position of tool 60 also varies: $\Delta z_1 \pm \Delta z_2$. To maintain $\Delta z_1$ constant, for example at about ⅔ of the alignment support angle Θ variation as shown in FIG.6b, the microcomputer 16 feedback control offsets the effect of $\Delta Z_2$ on $\Delta z_1$ by adjusting the fluid volummes in main cylinder chamber E and chamber F.

In FIG. 6a through FIG. 6c, $\Delta z_2$ (angle Θ) remains constant. Chamber E fills, chamber F empties, and increases $\Delta z_1$ from 0 (minimum), as shown in FIG. 6a, to 1 (maximum), as shown in FIG. 6c. Filling chamber F and emptying chamber E begins a return to the values shown in FIG. 6a. In FIG. 6b, consider that $\Delta z_1$ has an assigned value of ⅔ of the maximum value of the range between 0 and 1.

In summary, as shown in FIGS. 2 through FIG. 6, sliding elements within the transporter housing 40 and sub-cylinder 22 control the tool 60 location in the X-Y plane ($\Delta xy$ and angle $\Theta/\Delta z_2$). Vertical movement of sub-cylinder 22 within cylinder 20 control their location along the Z-axis ($\Delta z_1$). The coordinated movements of all moveable platform components (the alignment support 30, sub-cylinder 22 and the central slide complex 40, 50) determine the path of tool 60, $F_D(x,y,z)$ for a drill and $F_s(x,y,z)$ for the scanner. To coordinate these movements, the microcomputer 10 sends signals to pumps 15-R, 15-S and 15-T.

Stated another way, the fluid control systems and the microcomputer 16 determine angle Θ ($\Delta z_2$) and $\Delta z_1$ so that the platform carrying the scanner and/or working tool implement accurately follow a predetermined path for a specific application. Each application of the scanner and driller requires different controls on angle Θ ($\Delta z_2$) and $\Delta z_1$. Also, for specific applications, several possible modifications in the platform's design include: customized sensors for special applications; a universal joint between, for example, the transporter housing 40 and the mount 20; a universal joint between the scanner or drill mount, the alignment support, or the support brace. Also, a single platform can have multiple stationary cylinders 20, each with a separate alignment support 30 and transporter housing 40. An alignment support can have multiple transporter housings and a transporter housing can have multiple central slide complexes 46, 50. Further, a central slide complex can have multiple mounts 50.

In a typical dental application the system is located in the mouth of a patient and the suspect tooth is scanned tomographically. Using the microcomputer, the dentist aligns the scanner above the tooth. The computer is programmed to suggest or carry out a scanning protocol in which it moves in the path $F_s(x,y,z)$ and the scanner scans the tooth's surface and subsurface anatomy. Sensors are located, for example, in the scanner and on other parts of the base, transporter housing, etc., in accordance with the type of scanner being used.

On a high resolution monitor, the dentist reviews computer-generated images of the tooth that was scanned. The reflectivity of a tooth's layers (enamel, dentin and nerve) is different and quantifiable. The dental scanner, sensors (detector electronics) and reconstruction algorithms of the computer generate an accurate tomographic dental image that distinguishes healthy and unhealthy dental layers. Besides distinguishing a bruised nerve from an irreversibly damaged nerve, the scanner image accurately identifies many previously unseen details: small cavities in the enamel, fractures in the enamel, dentin and dental root, small areas of root resorption (internal and external), calcific (sclerotic) changes, and bone loss (periodontal disease). Also, the tomographic image identifies potentially harmful microfractures in the enamel and dentin. Although small, these microfractures are clinically significant and are not seen either clinically or on conventional two-dimensional dental X-rays.

By using a suitable computer interface system, such as a GUI (Graphic User Interface), the dentist enters a drilling design on the computer screen image and activates the drill. The drill tools (mills and drills) the same design in the tooth that appears on the computer monitor screen. In a typical drilling of a tooth the system controls the drill tool 60 in the path $F_D$. The movement $F_D(x,y,z)$ requires a combination drilling-and-milling procedure. During $F_D(x,y,z)$ for a large molar tooth, for example, $\Delta z_1$ varies from 0 inches to 0.375 inches, angle Θ varies from 0 degrees to 180 degrees, and $\Delta xy$ varies from 0 inches to 0.625 inches. As angle Θ varies from 0 degrees to 180 degrees, $\Delta Z_2$ varies from, for example, 0 inches to 0.010 inches. Additionally, because angle Θ is a function of $\Delta z_2$, rotational tolerances for angle e convert to the linear tolerance for $\Delta z_2$, for example, ±0.001 inches.

A typical drill can be, for example, a variable speed (maximum 350,000 RPM) air-turbine drill. Engaged in the drill is a parallel-sided #57 bur. This bur is aligned to mill and drill parallel to the Z axis of the tooth. When aligned parallel to the Z axis, the bur removes decay associated with the occlusal/incisal or chewing surface of teeth. Sometimes, clinical needs (cavities) for tooth removal require drilling only on the gum line (gingival crest)-no drilling is required on the occlusal/incisal surface of the tooth. When gum line cavities need a restoration, the dentist uses a modified procedure in which the same #57 bur is inserted in the same drill housing. However instead of insertion parallel to the Z axis, the #57 bur is inserted perpendicular to the Z axis in the modified version of the drill. Other designs for drilling gum line cavities include use of a universal joint between the transporter housing and the drill gantry.

Dental records of diagnostic findings and restorative treatment can be maintained on magnetic storage media such as a floppy disc or a hard-drive and there is no need for dental X-ray film. A modem can be used to transmit diagnostic and treatment information to, for example, dental laboratories. Hard copies of dental records can be printed out from the storage medium.

I claim:

1. A system for positioning a tool in a first plane and in a direction generally orthogonal to said first plane relative to a three-dimensional object to be worked on by the tool comprising:

a mount for supporting a tool;

a first support generally parallel to said first plane;

first positioning means associated with said first support for moving said mount in said first plane relative to said first support;

a second support extending in said orthogonal direction to which said first support is coupled;

second positioning means associated with said second support to move said second support and said first support coupled thereto in said orthogonal direction;

third positioning means associated with said second support to rotate said second support and said first support coupled thereto; and control means comprising a computer for setting the movement of said first, second and third positioning means to position the tool supported on said mount to a selected position of said first plane and at a selected distance from said first plane in said orthogonal direction on or into the object being worked on by the tool corresponding to locations on a tomographic image of the object.

2. A system as in claim 1 wherein said first support is an elongated arm and said first positioning means moves in either direction along said arm.

3. A system as in claim 2 wherein said first positioning means comprises a slide within said arm to which said mount is coupled, said slide being moved along said arm.

4. A system as in claim 3 wherein said first positioning means further comprises a fluid chamber on each side of said slide, said control means operating to establish the fluid volume in said chambers to position said slide and said mount along said arm.

5. A system as in claim 3 wherein said second positioning means comprises a main cylinder, a piston in said main cylinder to which said second support is coupled, a fluid chamber on each side of said piston in said main cylinder, and said control means operating to establish the fluid volume in each of said second positioning means chambers to move said piston and said second support means with said arm coupled thereto in said orthogonal direction.

6. A system as in claim 5 wherein said third positioning means comprises a sub-cylinder within said piston, a fluid chamber in said piston on each side of said sub-cylinder, said control means operating to establish the fluid in each chamber of said piston to move said sub-cylinder in said orthogonal direction, and means for converting the orthogonal direction movement of said sub-cylinder to rotational movement to rotate said second support and said first support coupled thereto.

7. A system as in claim 6 wherein said means for converting comprises a helical thread on one of said sub-cylinder and said piston and a pawl on the other of said sub-cylinder and piston engaging said thread cooperating to rotate said sub-cylinder and said second support coupled thereto as said sub-cylinder is moved in the orthogonal direction.

8. A system as in claim 1 wherein said third positioning means converts linear motion to rotary motion.

9. A method of diagnosing and treating a tooth of a subject comprising the steps of:

forming a tomographic image of the tooth;

placing a positioning system having a tool mount in the mouth of the subject; and operating said positioning system in response to said tomographic image with said mount including a treating tool to position the treating tool on or in the body of the tooth to treat the tooth.

10. A method as in claim 9 wherein said forming step comprises operating said positioning system with said mount including a scanner for scanning the tooth for acquiring the data for forming said tomographic image.

11. A method as in claim 9 wherein said step of operating said positioning system further comprises operating said positioning system with said mount including either a scanner or a treating tool and positioning said mount in a first plane and in a direction generally orthogonal to said first plane.

12. A method as in claim 11 wherein the step of positioning said mount further comprises;

providing a first support generally parallel to said first plane;

moving said mount in either direction along said first support;

providing a second support extending in said orthogonal direction to which said first support is coupled;

moving said second support and said first support mounted thereto in said orthogonal direction; and rotating said second support and said first support coupled thereto.

13. A system for positioning a tool in a first plane and in a direction generally orthogonal to said first plane relative to an object being worked comprising:

a mount for supporting a tool;

a first support comprising an elongated arm generally parallel to said first plane;

first positioning means comprising a slide associated with said first support for moving said mount in said first plane in either direction along said first support and a fluid chamber on each side of said slide;

a second support extending in said orthogonal direction to which said first support is coupled;

second positioning means associated with said second support to move said second support and said first support coupled thereto in said orthogonal direction;

third positioning means associated with said second support to rotate said second support and said first support coupled thereto; and control means operating to establish the fluid volume in said chambers to position said slide and said mount along said arm for setting the movement of each of said first positioning means and for setting the position of said second and third positioning means to position said mount and the supported tool to a selected position of said first plane and at a selected distance from said first plane in said orthogonal direction.

14. A system as in claim 13 wherein said third positioning means converts linear motion to rotary motion.

15. A system as in claim 13 wherein said second positioning means comprises a main cylinder, a piston in said main cylinder to which said second support is connected, a fluid chamber on each side of said piston in said main cylinder, and said control means operating to establish the fluid volume in each of said second positioning means chambers to move said piston and said second support means with said arm coupled thereto in said orthogonal direction.

16. A system as in claim 15 wherein said third positioning means comprises a sub-cylinder within said piston, a fluid chamber in said piston on each side of said sub-cylinder, said control means operating to establish the fluid in each chamber of said piston to move said sub-cylinder in said orthogonal direction, and means for converting the orthogonal direction movement of said sub-cylinder to rotational movement to rotate said second support and said first support coupled thereto.

17. A system as in claim 16 wherein said means for converting comprises a helical thread on one of said sub-cylinder and said piston and a pawl on the other of said sub-cylinder and piston engaging said thread cooperating to rotate said sub-cylinder and said second support coupled thereto as said sub-cylinder is moved in the orthogonal direction.

18. A system as in claim 13 further comprising a scanner coupled to said mount as said tool.

* * * * *